(12) United States Patent
Lakkis et al.

(10) Patent No.: US 8,588,284 B2
(45) Date of Patent: *Nov. 19, 2013

(54) SYSTEMS AND METHODS FOR NETWORKED WEARABLE MEDICAL SENSORS

(75) Inventors: Ismail Lakkis, San Diego, CA (US); Hock Law, San Diego, CA (US)

(73) Assignee: Adeptence, LLC, Los Angeles, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 13/151,248

(22) Filed: Jun. 1, 2011

(65) Prior Publication Data

US 2011/0295102 A1    Dec. 1, 2011

Related U.S. Application Data

(60) Provisional application No. 61/350,439, filed on Jun. 1, 2010.

(51) Int. Cl.
*H04B 1/38* (2006.01)
(52) U.S. Cl.
USPC ........... 375/220; 375/316; 375/295; 375/219; 375/222; 375/354; 375/356; 375/359; 375/362; 375/363; 375/364; 375/365; 375/366; 375/367; 375/368
(58) Field of Classification Search
USPC ......... 375/316, 295, 219, 220, 222, 354, 356, 375/359, 362, 363, 364, 365, 366, 367, 368
See application file for complete search history.

(56) References Cited

U.S. PATENT DOCUMENTS

| | | | | |
|---|---|---|---|---|
| 5,892,757 A * | 4/1999 | Norrell et al. | ................. | 370/292 |
| 6,466,125 B1 | 10/2002 | Richards et al. | | |
| 8,081,072 B2 * | 12/2011 | Scalisi et al. | ............. | 340/539.13 |
| 8,152,053 B2 * | 4/2012 | Pietrzyk et al. | ................ | 235/375 |
| 2007/0060976 A1 | 3/2007 | Denzene et al. | | |
| 2009/0051544 A1 | 2/2009 | Niknejad | | |
| 2009/0163772 A1 | 6/2009 | Koide et al. | | |
| 2010/0234693 A1 * | 9/2010 | Srinivasan et al. | ............. | 600/300 |
| 2012/0002702 A1 * | 1/2012 | Lakkis et al. | ................ | 375/130 |

OTHER PUBLICATIONS

International Search Report and Written Opinion issued in PCT/US2011/038827 on Feb. 17, 2012, 9 pages.

* cited by examiner

*Primary Examiner* — Siu Lee
(74) *Attorney, Agent, or Firm* — Procopio, Cory, Hargreaves & Savitch LLP; Noel C. Gilliespie

(57) ABSTRACT

A medical sensor system comprises a gateway comprising a wideband receiver and a narrow band transmitter, the each gateway configured to receive a wideband positioning frame using the wideband receiver from one or more wearable sensors and to transmit acknowledgement frames using the narrow band transmitter that include timing and control data for use by the sensors to establish timing for transmission of the positioning frame; and at least one wearable sensor comprising a wideband transmitter and a narrow band receiver, the sensor configured to transmit a sensor data frame to the gateway using the wideband transmitter and to receive an acknowledgement frame from the gateway using the narrow band receiver, extract timing and control information from the frame, and adjust the timing and synchronization of the wideband transmitter using the timing and control information.

13 Claims, 17 Drawing Sheets

Basic Core

SYSTEMS AND METHODS FOR NETWORKED WEARABLE MEDICAL SENSORS

RELATED APPLICATION INFORMATION

This application claims priority under 35 U.S.C. 119(e) to U.S. Provisional Patent Application Ser. No. 61/350,439, file Jun. 1, 2010, and entitled "Networked Wearable Medical Sensors," which is Incorporated herein by reference in its entirety as if set forth in full.

BACKGROUND

1. Technical Field

The embodiments described herein are related to wireless communication and in particular to systems and methods for medical sensors that can sense a plurality of vital signs and that can provide imaging within the body.

2. Related Art

Remote monitoring in health and medical applications is becoming more and more common and may hold the key to reversing the health spending curve in the the United States and other nations. Remote monitoring, m-health, wireless health, etc., applications may also lead to improved care and better preventative care. There are numerous conditions, events, situations, etc., where adequate remote monitoring could prevent unwarranted trips to the hospital, emergency room, doctor's office, etc., and that could allow patients to stay at home instead of being in a hospital.

For example, fetal monitoring systems could allow an expecting mother to remain at home while the babies heart rate and mother's contraction are being monitored in certain situations, rather than the mother having to go to the hospital for such monitoring when it is really not necessary. Patients can be better monitored after discharge after surgery or a traumatic event like a heart attack, brain injury, or stroke. Thus, preventing re-admittance or trips to the hospital that are not necessary and also identifying conditions or behaviors that do necessitate a trip to the hospital or doctor's office.

Micropower Impulse Radar systems have also been developed that can enable low power, low cost sensors and imaging devices. Conventional radar sends out short bursts of single-frequency (narrowband) electromagnetic energy in the microwave frequency range. Other radars step through multiple (wideband) frequencies to obtain more information about a scene. An impulse, or ultrawide-band, radar such as MIR sends individual pulses that contain energy over a very wide band of frequencies. The shorter the pulse, the wider the band, thereby generating even greater information about reflected objects. Because the pulse is so short, very little power is needed to generate the signal. MIR is unique because it inexpensively generates and detects very fast (subnanosecond) pulses. The drawback of using short, low-power pulses is that less energy can be measured on the radar returns. This problem can be solved by transmitting many pulses rapidly and averaging all returns.

The advantages of producing and detecting very brief radar impulses are considerable:

The target echoes return much information. With short pulses, the system operates across a wide band of frequencies, giving high resolution and accuracy. The system is also less susceptible to interference from other radars.

Battery current is drawn only during the short time the system is pulsed, so power requirements are extremely low (microamperes). One type of MIR conventional unit operates for several years on two AA batteries.

The microwave power associated with pulsed transmission is exceedingly low (averaging tens of microwatts) and is medically safe. MIR emits less than one-millionth the power of a cellular telephone.

FIG. 1 is a diagram illustrating an example, conventional MIR circuit developed by Lawrence Livermore Laboratories. The circuit of FIG. 1 can be used in a MIR motion sensor. In the MIR motion sensor, a transmitting antenna radiates a pulse that is about 0.2 nanoseconds long. Reflections from targets return a complex series of echoes to the receiving antenna. The return signal is sampled at one range-gate time by an impulse receiver containing a voltage sampler along with an averaging circuit and amplifier. The detector listens at the appropriate time for an echo. For an object about 3 m from the MIR, the sampled gate at 20 nanoseconds after transmission would just capture it.

Because the wavelength of MIR signals in a conventional system in air is currently about 15 cm, objects can easily be detected that are of about that size or larger at distances of about 15 cm or greater. Distorted, low-amplitude reflections of the transmitted pulse are picked up by the receiving antenna in the time it takes for light to travel from the MIR to the object and back again.

The operating principle of MIR motion sensors illustrated in FIG. 1 is based on the relatively straightforward principle of range gating. In looking for the return signals, MIR samples only those signals occurring in a narrow time window after each transmitted pulse, called a range gate. If we choose a delay time after each transmitted pulse corresponding to a range in space, then we can open the receiver "gate" after that delay and close it an instant later. In this way, we avoid receiving unwanted signals.

The MIR receiver has a very fast sampler that measures only one delay time or range gate per transmitted pulse, as shown in FIG. 2A. In fact, circuitry can be used that is similar to the transmit impulse generator for this range-gated measurement, another unique feature of our device. Only those return pulses within the small range gate corresponding to a fixed distance from device to target-are measured. The gate width (the sampling time) is always fixed based on the length of the pulse; but the delay time (the range) is adjustable, as is the detection sensitivity. Averaging thousands of pulses improves the signal-to-noise ratio for a single measurement; i.e., noise is reduced, which increases sensitivity. A selected threshold on the averaged signal senses any motion and can trigger a switch, such as an alarm.

A noise source is intentionally added to the timing of the circuitry in FIG. 1 so that the amount of time between pulses varies randomly around 2 MHz. There are three reasons for randomizing the pulse repetition rate and averaging thousands of samples at those random times. First, interference from radio and TV station harmonics can trigger false alarms; but with randomizing, interference is effectively averaged to zero. Second, multiple MIR units can be activated in one vicinity without interfering with each other if the operation of each unit is randomly coded and unique. Each unit creates a pattern recognizable only by the originating MIR. Third, randomizing spreads the sensor's emission spectrum so the MIR signals resemble background noise, which is difficult for other sensors to detect. Emissions from an MIR sensor are virtually undetectable with a conventional radio-frequency receiver and antenna only 3 m away. In other words, randomizing makes the MIR stealthy.

More sophisticated MIR sensors, such as our MIR Rangefinder, cycle through many range gates. As shown in FIG. 2B, the delay time is swept, or varied, slowly with each received pulse (about 40 sweeps per second) to effectively fill in the detection bubble with a continuous trace of radar information. In essence, we are taking samples at different times, thus different distances, away from the device. The result is an "equivalent-time" record of all return pulses that can be correlated to object distance. The equivalent-time echo pattern exactly matches the original "real-time" pattern, except that it occurs on a time scale slowed by 106.

Referring to FIG. 2A, following an impulse transmitted by MIR, a range gate opens briefly after a fixed delay time to sample the received radar echoes. In FIG. 3B it can be seen that to obtain a more complete record of returns for more sophisticated applications, we sweep the range delay over various delay times to obtain target information at different distances. The radar signal has then been effectively slowed down by about a factor of 1 million to get an "equivalent-time" record of radar returns that can be correlated to object distances.

As conventional MIR technology has evolved, a unique combination of features has resulted. Although certain specifications-signal strength, operating range, and directionality can vary depending on the type of system and its intended purpose, the following features are common to most conventional units:

Low cost, using off-the-shelf components.

Very small size (circuit board is about 4 cm2).

Excellent signal penetration through most low-conductivity materials, so it is able to "see through" walls, concrete, and other baniers, including human tissue.

A sharply defined and adjustable range of operation, which reduces false alarms.

Long battery life, typically several years, because of micropower operation.

Simultaneous operation of many units without interference.

Randomized emissions, making the sensor difficult to detect.

Current MIR prototype units at LLNL are made with low-cost, discrete components. In the planning stages are single chips-application-specific integrated circuits (ASICs)-that will replace most of the discrete parts and result in even lower co t and smaller size. One limitation is that the penetration of MIR signals through a material decreases as that material's electrical conductivity increases. Thus, the MIR technology opens up many possible low-cost sensor systems for motion detection or proximity, distance measurement, microwave image formation, or even communications. For example, in some cases it has advantages over many kinds of conventional proximity and motion sensors, such as passive infrared (heat sensors), active beam-interruption infrared, ultrasound, seismic, and microwave Doppler devices.

Many of these sensors are adversely affected by temperature, weather, and other environmental conditions, making them prone to false alarms. Passive infrared sensors can be triggered by light and heat, and their detection range is not well defined. Even a thin sheet of paper blocks both infrared and ultrasound signals. Similarly, ultrasound motion and Doppler microwave sensors interfere with one another when several units are co-located. Without range gates, these sensors can trigger as easily on distant objects as on nearby insects. They can also have limited material penetration, detectable emissions, and expensive components. MIR technology provides an attractive alternative to these devices.

Further, a conventional MIR's average emission level is about a microwatt-about 3 order of magnitude lower than most international standard for continuous human exposure to microwave. Thus, MIR is a medically harmless diagnostic tool. This can enable sensors that can remotely measure human vital signs, without interfering with computer, digital watches, FM radio, or television.

For example, a MIR heart monitor can measure muscle contractions (response of the heart) rather than the electrical impulse (stimuli) measured with an electrocardiogram (EKG). FIG. 3 shows the output waveform of a prototype heart monitor compared to that obtained from a standard EKG. The MIR output is complex and rich in detailed information. As a medical monitor, a very small MIR unit built into a single chip could substitute for a stethoscope.

A portable device can then be developed that could be worn inside clothing so an individual's vital sign can be relayed from a remote location to a medical office or hospital.

An MIR-based breathing monitor can also be developed, see the ouput waveforms in FIG. 4 that does not have to make contact with a person's body. Rather, such a monitor could operate through a mattress, wall, or other barriers. The detection of breathing motion can be a valuable asset in hospitals and homes, could guard against sudden-infant-death syndrome, and might be used by people with breathing disorders such as sleep apnea, in which the affected individual occasionally stops breathing.

Additional potential medical devices that can take advantage of MIR technology include speech-sensing devices and a polygraph sensor. Devices for the blind could warn of obstacles and variations in terrain and help to train individuals in using canes.

One problem with conventional MIR technology is that it is still too high power to really enable a wide range of remote medical monitoring applications. In many instances, a remote sensor would be very small, very light weight, very low costs, and likely a throw away device. Moreover, there currently is not system that integrates MIR medical and imaging sensor data with other vital sign data such as temperature.

SUMMARY

Methods for low power, low cost, throw away, integrated medical sensor systems are described herein.

According to one aspect, a medical sensor system comprises a gateway comprising a wideband receiver and a narrow band transmitter, the each gateway configured to receive a wideband positioning frame using the wideband receiver from one or more wearable sensors and to transmit acknowledgement frames using the narrow band transmitter that include timing and control data for use by the sensors to establish timing for transmission of the positioning frame; and at least one wearable sensor comprising a wideband transmitter and a narrow band receiver, the sensor configured to transmit a sensor data frame to the gateway using the wideband transmitter and to receive an acknowledgement frame from the gateway using the narrow band receiver, extract timing and control information from the frame, and adjust the timing and synchronization of the wideband transmitter using the timing and control information.

These and other features, aspects, and embodiments are described below in the section entitled "Detailed Description."

BRIEF DESCRIPTION OF THE DRAWINGS

Features, aspects, and embodiments are described in conjunction with the attached drawings, in which.

DETAILED DESCRIPTION

The embodiments described herein relate to a wireless system sensor architecture that includes small, inexpensive, disposable, long lasting wearable medical sensors and MIR type imaging sensors that are also small, inexpensive, disposable, and long lasting.

Figure 1:
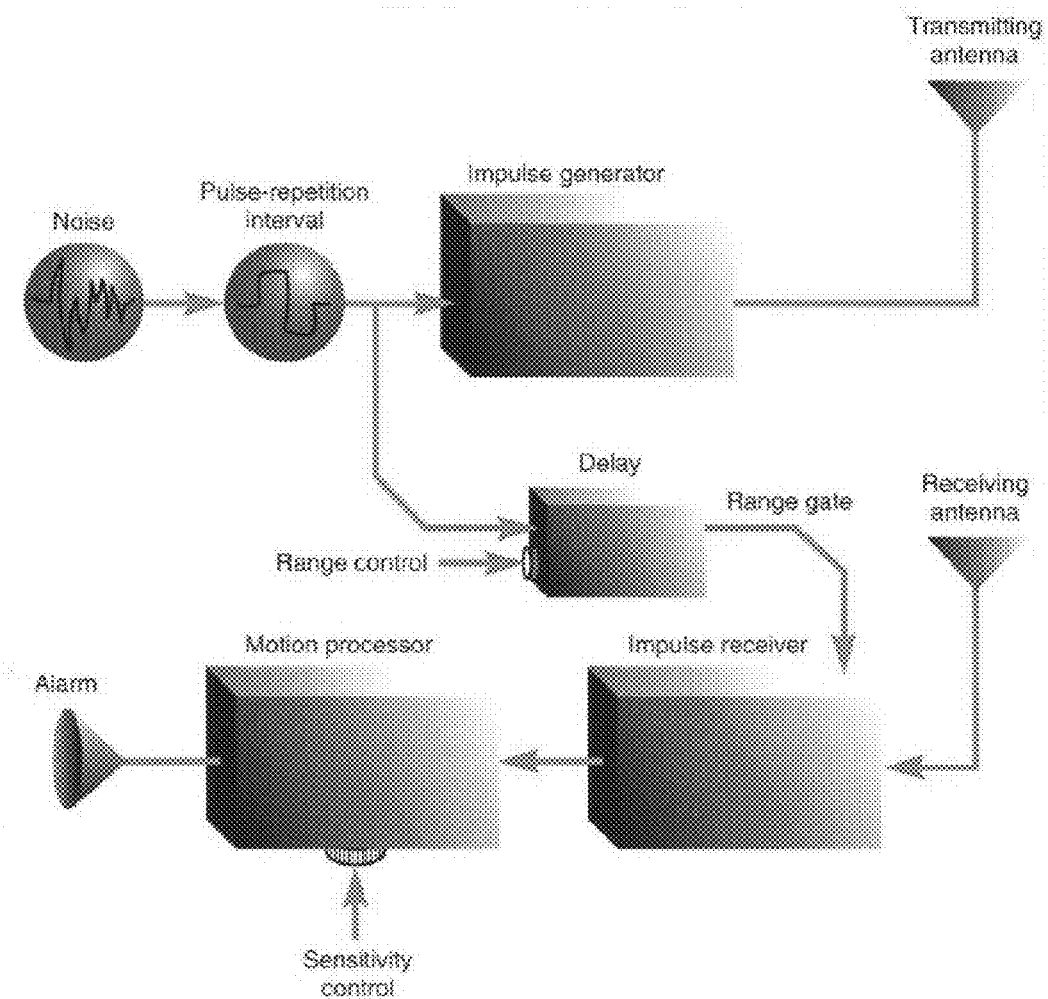
FIG. 1 is a diagram illustrating a conventional MIR circuit.
Figure 2A:
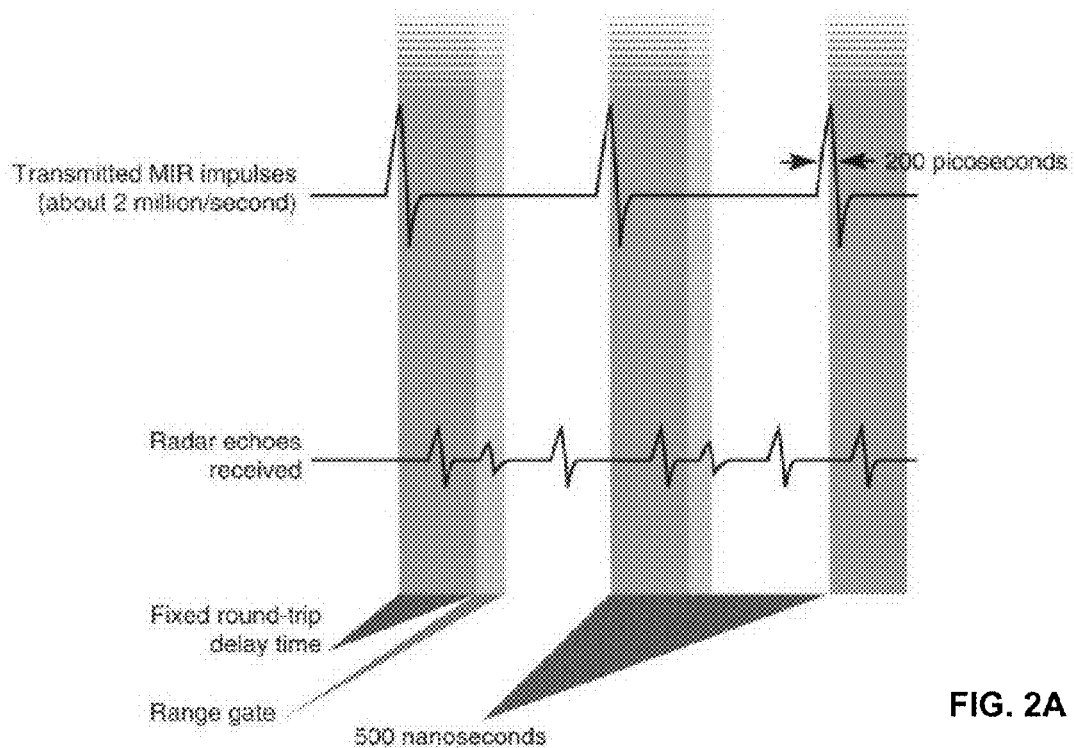
FIG. 2A is a diagram illustrating example transmission pulses and received echoes in the system of FIG. 1.
Figure 2B:
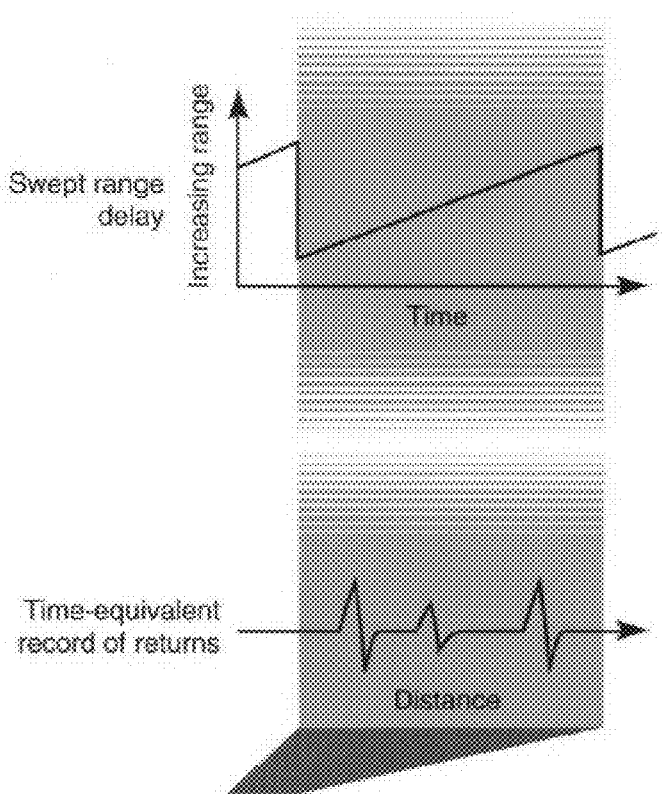
FIG. 2B is a diagram illustrating an example sweep range delay implemented in the system of FIG. 1.
Figure 3:
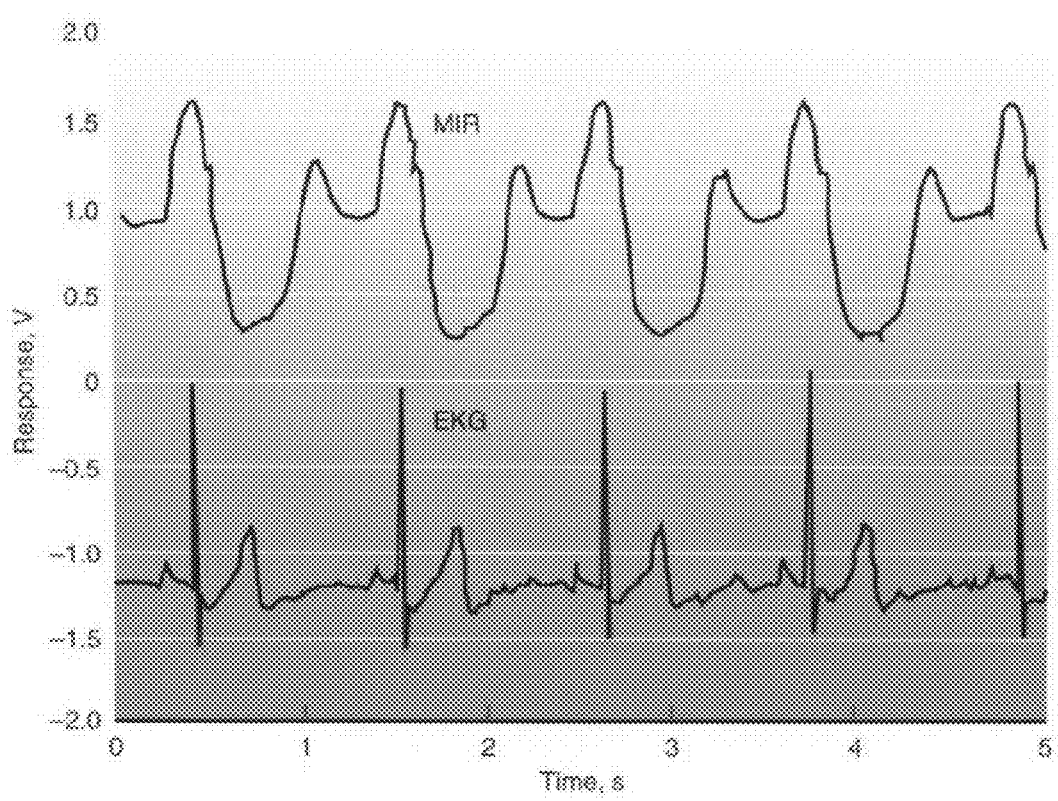
FIG. 3 is a diagram illustrating a comparisons between the waveforms of a MIR heart monitor and an EKG.
Figure 4:
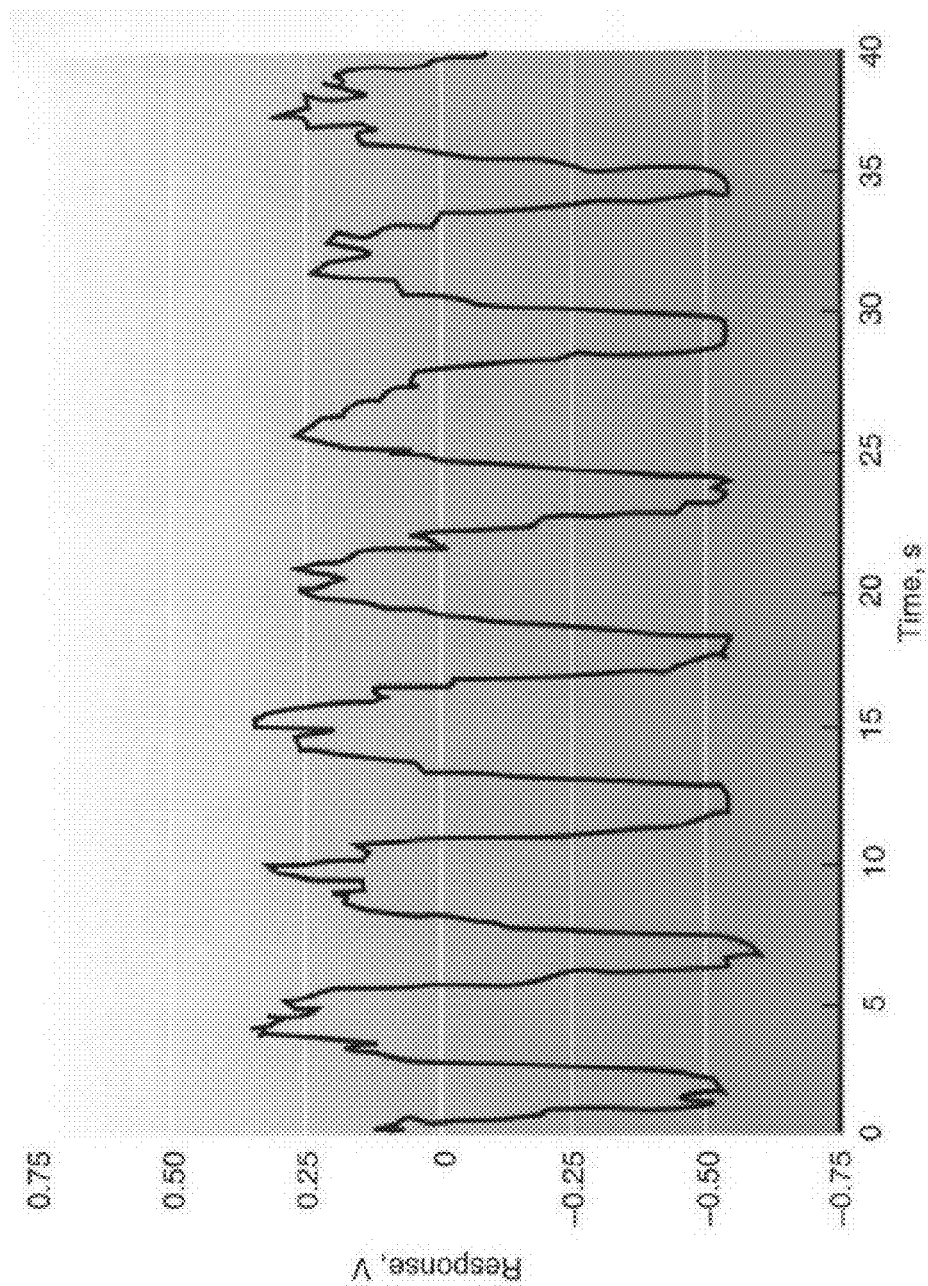
FIG. 4 is a diagram illustrating the waveforms of a MIR breathing monitor.
Figure 5:
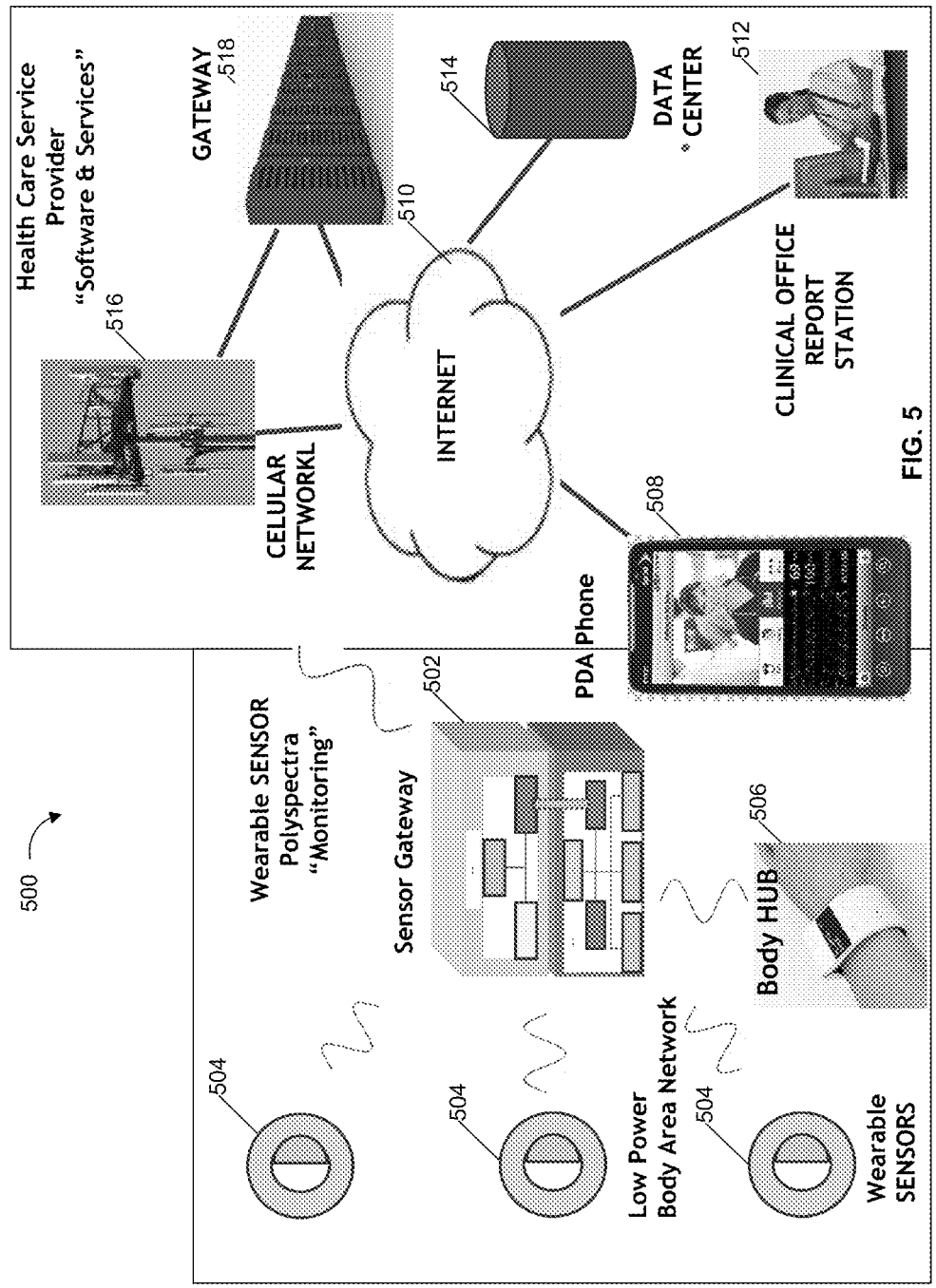
FIG. 5 is a diagram illustrating an example wireless sensor system in accordance with one embodiment.

FIG. 5 is a diagram illustrating an example wireless sensor system 500 in accordance with one embodiment. System 500 includes a sensor gateway that is configured to communicate with a plurality of wearable sensors 504 that can comprise a body area network. System 500 can also include a body hub 506, which can be configured to aggregate information from sensors 504 and then communicate the information to gateway 502. Gateway 502 can be configured to communicate information to one or more of a clinical office 512, data center 514, or gateway 518 either directly or through a communication device such as a mobile device 508. It certain embodiments, hub 506 can also communicate information with mobile device 508.

Mobile device 508 can comprise a PDA, tablet, smart phone, laptop, etc. Also, while not shown, the information from sensors 504 can also be communicated with a doctor, hospital, care giver, family member, payor, etc. Also, while not shown, system 500 can include a MIR type imaging device as described below.

Sensors 504 can be low cost, light weight, wearable sensors with long battery life. Thus, a number of such sensors can be worn by an individual and the data gathered, e.g., by hub 506, gateway 502, or both and then communicated as needed. By using communication, data extraction, and other techniques, the devices can be made very small. Some of these techniques are described in more detail below.

Figure 6:
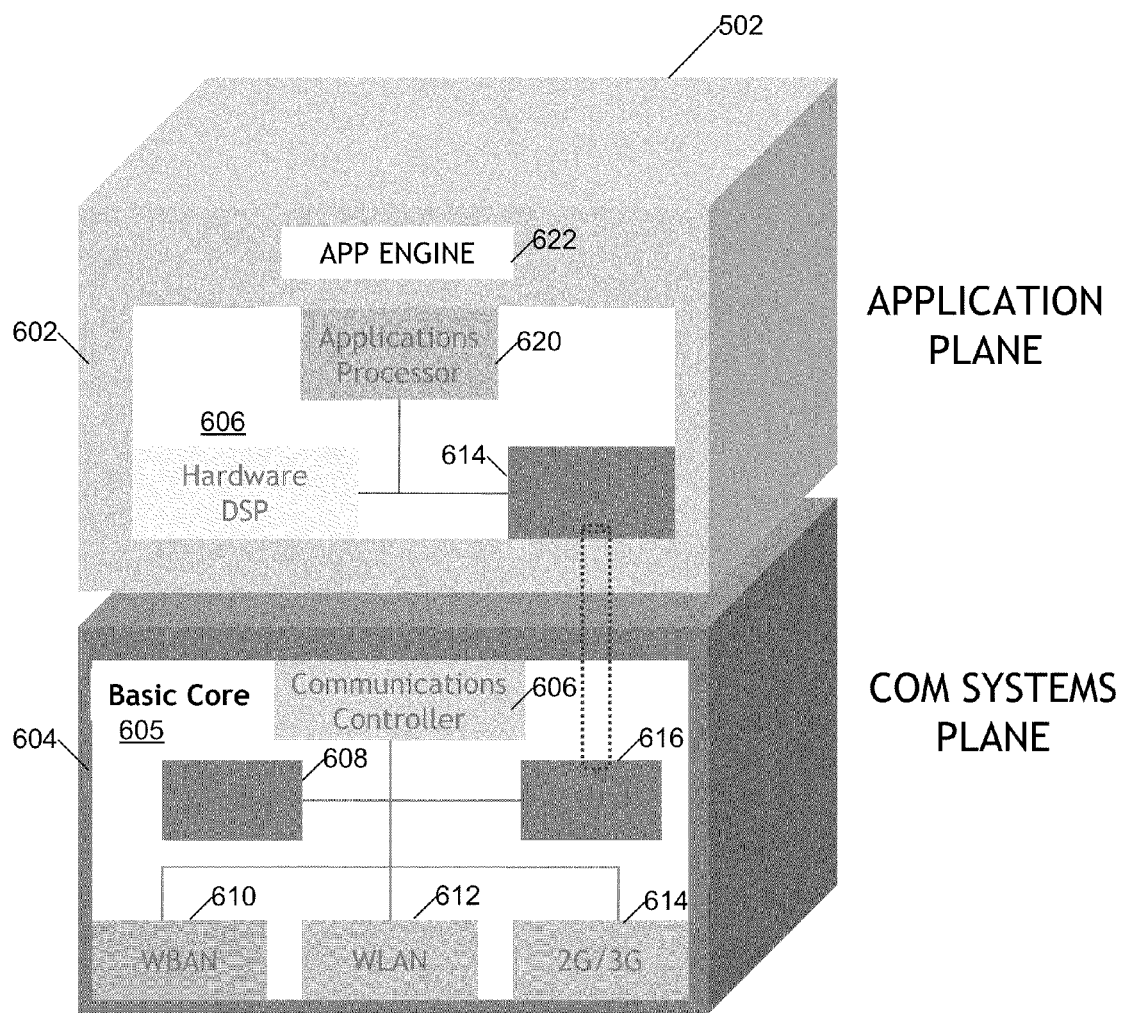
FIG. 6 is a block diagram illustrating an example gateway that can be included in the system of FIG. 5 in accordance with one embodiment.

FIG. 6 is a block diagram illustrating an example sensor gateway 502 in accordance with one embodiment. Gateway 502 can comprise an application plane 602 and a communication system plane 604. Communication system plane 604 can include a basic core 605 that includes communications controller 606, I/O 616 for communicating with the application plane 602, in certain embodiments display output 608, and communication interfaces 610-612.

Communication interfaces 610-612 allow gateway 502 to communicate with sensors 504, hub 506, mobile device 508, and network 516. Thus, for example, the communication interface 610 can include a Wireless Body Area Network (WBAN) communication interface 610, for communicating with sensors 504 and in certain embodiments hub 506; Wireless Local area Network (WLAN) communication interface 612 for communicating with mobile device 508 and in certain embodiments hub 506; and Wireless Wide Area Network (WWAN) communication interface 614 for communicating with network 516.

It will be understood that communication interfaces 610-614 can refer to the transceiver circuitry and antenna devices and circuitry needed to communicate with the various devices via these communication interfaces, some of which is described below.

In certain embodiments, WBAN communication interface can actually comprise a wideband receiver and a narrow band transmitter, which would normally be associated with a WLAN communication interface. In other embodiments, WBAN communication interface 610 can comprise a wideband receiver an also make use of a narrow band transmitter included in WLAN communication interface 612.

Figure 7:
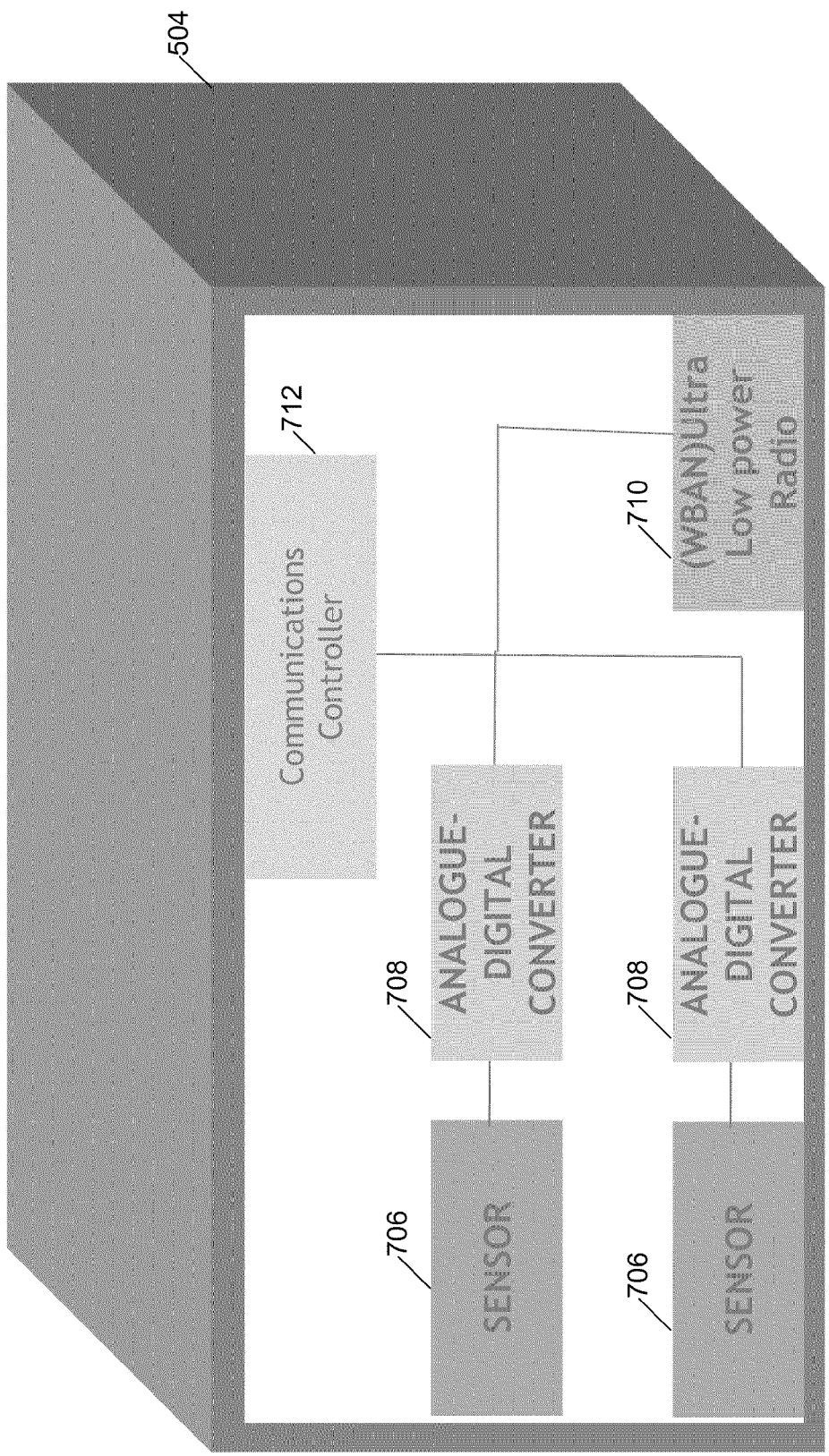
FIG. 7 is a block diagram illustrating an example wearable sensor that can be included in the system of FIG. 5.

FIG. 7 is a block diagram illustrating an example wearable sensor 504 in accordance with one embodiment. As can seen, sensor 504 can actually include one or more sensors 706. Typically these sensors would be some type of transducer that generates an analogue output related to a sensed, e.g., vital sign such as heart rate, respiration rate, temperature, pulse oximetry, blood pressure, electrocardiogram, amniotic fluid levels, etc. Analogue-to-digital converts 708 can then convert the analog signals into digital signals that can be transmitted to gateway 502 or hub 506 via WBAN communication interface 710 under the control of communications controller 712.

Figure 8:
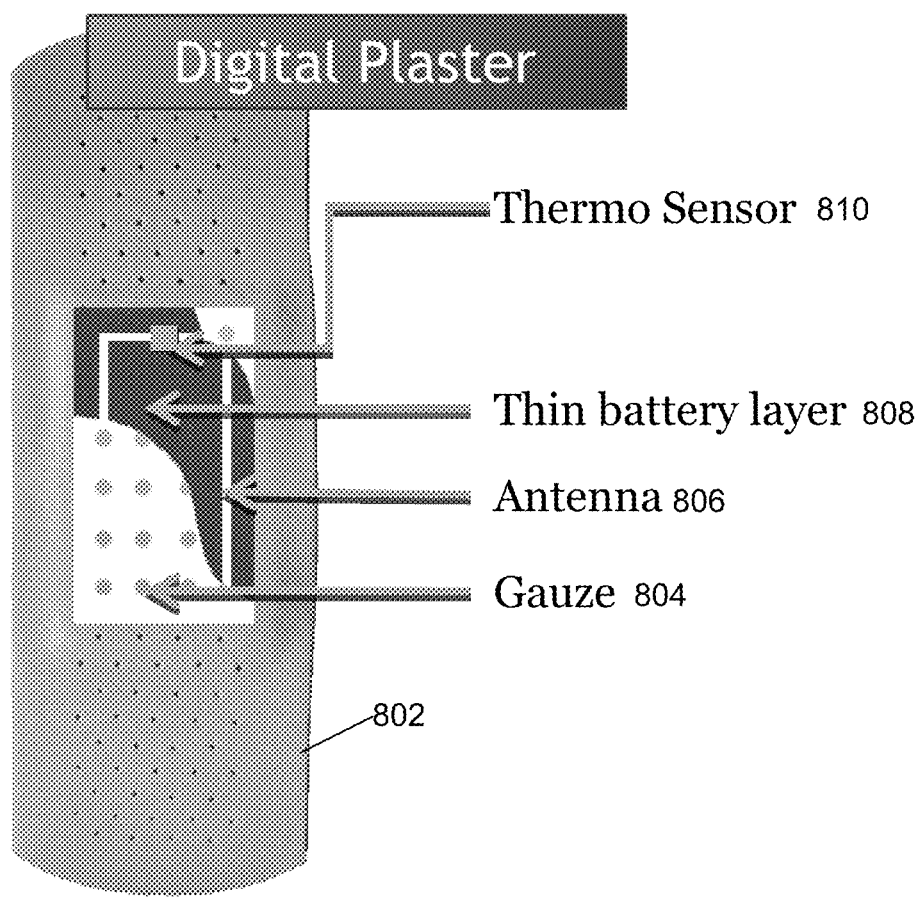
FIGS. 8 and 9 are diagrams illustrating example wearable sensors.
Figure 9:
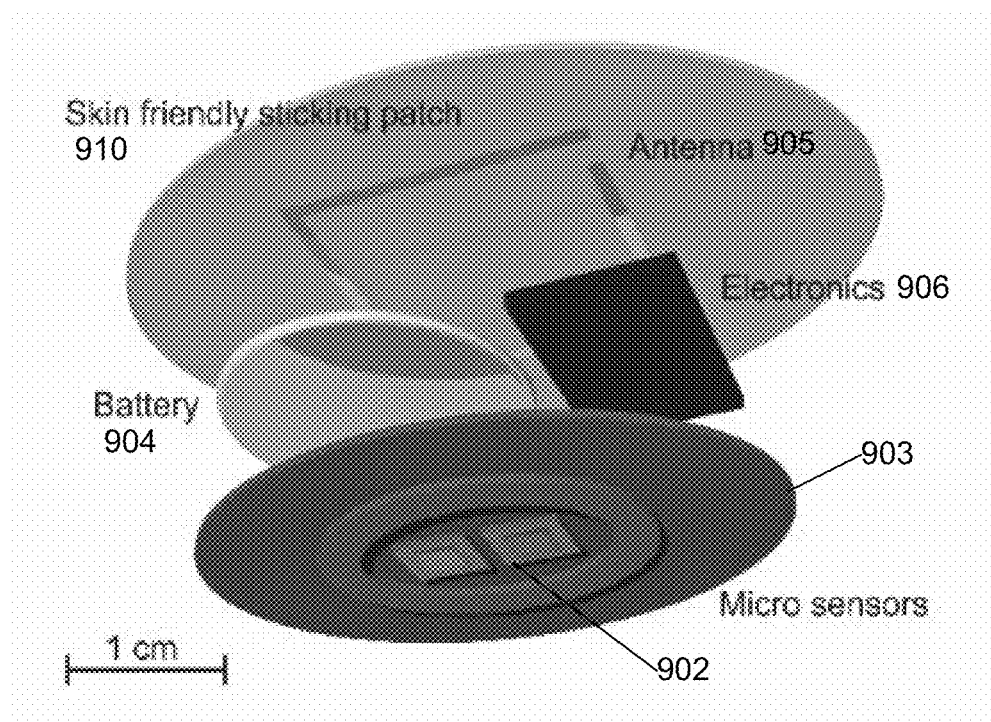

FIGS. 8 and 9 are diagrams illustrating example wearable sensors 504. In FIG. 8, the wearable sensor is a temperature sensor and is in the form of a normal Band-Aid. The sensor comprises gauze layer 804, antenna circuitry layer 806, thin battery layer 808, and thermo sensor layer 810. In certain embodiments, antenna layer 806, and battery layer 808 can be printed layers, i.e., the antenna and battery can both be printed. The sensor can also include a lower quality crystal, all of which reduces costs and size. But relatively large battery life times can be achieved using the techniques described below.

In certain embodiments, antenna layer 806, thin battery layer 808, and sensor layer 810, or some combination thereof can all be included in the same layer.

In FIG. 9, a small, wearable temperature sensor comprises micro sensors 902 on base layer 903, a battery 904, electronics 906, antenna 908, and adhesive layer 910. Again, antenna 908 and some or all of electronics 906 can be printed.

It can be seen that even though very small, even printable batteries are used in the example temperature sensors of FIGS. 8 and 9; however, long battery lives can be achieved even though the sensors can be configured for continuous monitoring. One way to achieve this is to us a wideband, e.g., UWB transmitter in WBAN communications interface 710 to communicate data to gateway 502, or possibly to hub 506. In fact, since communications interface 710 can be extremely low power, i.e., less than −10 db, the transmission distance will be short. This may necessitate the use of a hub 506.

As will be understood, a supeframe is generally used for UWB communications that requires relatively accurate timing, which is hard to provide with a lower quality crystal; however, gateway 502 or hub 506 can use a narrow band transmitter to transmit timing and other control information to the sensors 504. This means that WBAN interface 710 will also need to include a narrow band receiver to receive the narrow band control signals.

Because the gateway 502 can be fixed, e.g., within a building or room. Power is generally not a concern, so the gateway can transmit at very high power, e.g., up to 1 W. Further, the receiver included in WBAN interface 610, which is a wideband receiver configured to receive the wideband transmissions from the sensors 504, can be supplied with high power such that it can more easily detect and decode the very low power signals transmitted from the sensors 504.

The high power, narrow band transmitter in the gateway 502 can be used to transmit timing and synchronization information to the sensors 504 so that the sensors themselves do not require a high precision crystal. Thus they can be very low power, low cost, small devices that last for a long time without the need to replace a battery or the sensor 504. In fact, as mentioned, a printed battery can even be used in certain implementations.

Figure 10:
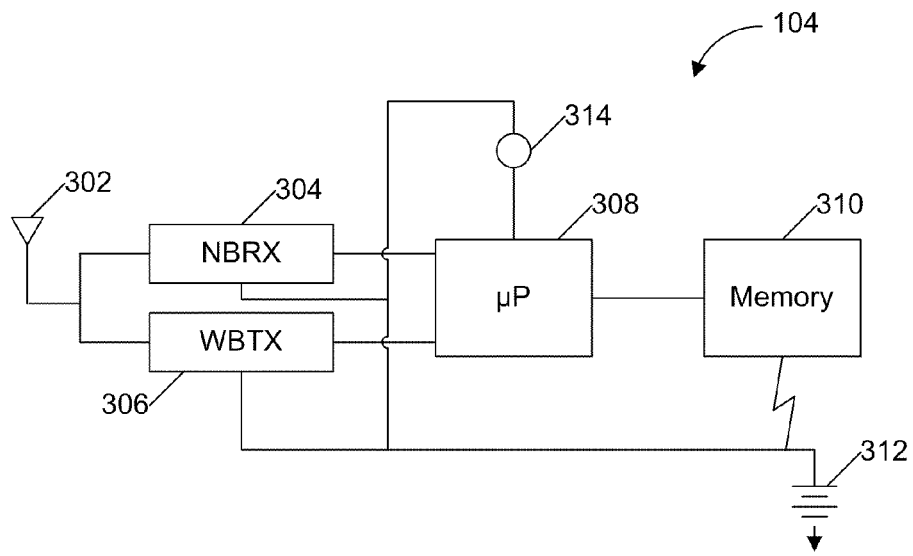
FIG. 10 is a block diagram illustrating an example wearable sensor that can be included in the system of FIG. 5.
Figure 11:
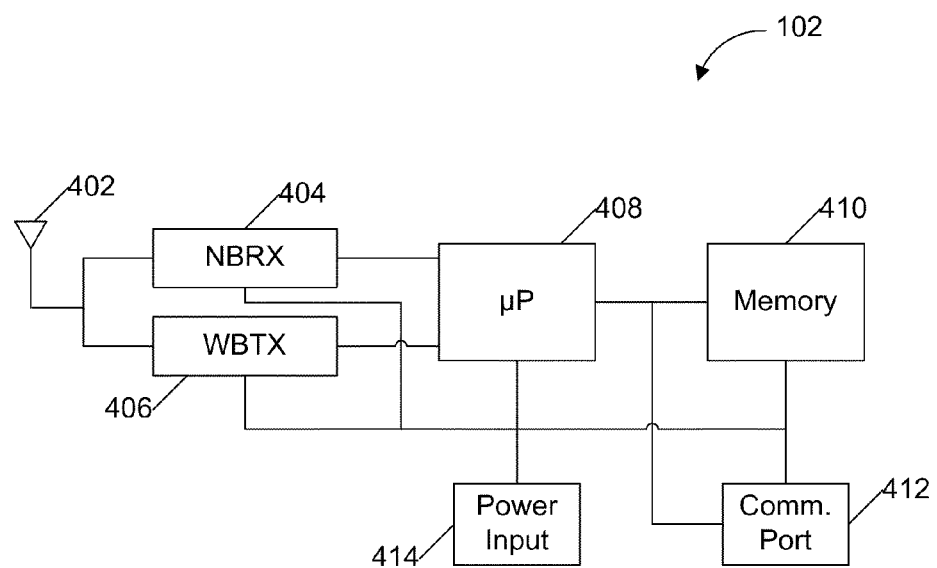
FIG. 11 is a block diagram illustrating an example gateway that can be included in the system of FIG. 5.

FIG. 10 is a block diagram illustrating an example sensor 504 in more detail and in accordance with another embodiment. Sensor 504 can comprise an antenna 302 configured to transmit wideband signals and receive narrow band signals. In certain embodiments, sensor 504 can comprise two antennae, one for receiving and one for transmitting. But because very precise timing can be used, sensor 504 does not need to transmit and receive at the same time. Thus, a single antenna can be used, reducing complexity, size, cost, etc.

Antenna 302 is then interfaced with wideband transmitter 304 and narrow band receiver 306. It will be understood that transmitter 304 can comprise the circuitry required for transmission. For example, transmitter 304 can comprise the filters, pulse shapers, modulators, amplifiers, digital to analog converters, etc., required for a specific transmitter design. Of course, transmitter 304 is a very low power transmitter, thus there is no need for a high power amplifier. Moreover, low power, all digital ultra wideband transmitter designs exist. Similarly, receiver 306 can comprise all of the circuitry required to receive the narrow band communications from gateway 502.

Transmitter 304 and receiver 306 can be interfaced with a processor or microcontroller 308 that can be configured to control the operation of sensor 504, decode information included on signals received by receiver 306, and generate information to be transmitted using transmitter 304. Processor 308 can be interfaced with memory 310, which can store instruction for processor 308 and data, such as an identifier, sensor data, etc. In many applications, a very limited amount of data is communicated, thus limiting the memory requirements.

A crystal 314 can also be included to control the timing of processor 308. As noted above, the crystal 314 can be a very inexpensive, low power crystal as a result of the systems and methods described herein.

It should also be noted that sensor 504 does not require a lot of power in the receiver, because gateway 502 can transmit at very high power, which can aid the ability of sensor 504 to receive and effectively decode the received narrow band signals.

Additionally, a power source 312 can be included and can be configured to power the components included in sensor 504. Power source 312 is often a battery, but because sensor 504 uses very low power for transmission, power source 312 does not have to have a large capacity in order to provide a relatively long lifetime. In fact, in certain embodiments, power source 312 can be a printed battery.

It should also be noted that antenna 302 can also be printed. In general, sensor 504 can be constructed as, or included in a sticker or Band-Aid, such as illustrated in FIGS. 8 and 9. Certainly, the ability to use a print battery allows for the reduction of potential layers and overall size of the sensor 504.

FIG. 110 is a block diagram illustrating an example gateway 502 according to another embodiment. As can be seen, the diagram of gateway 502 is very similar to that of sensor 504; however, gateway 502 includes a narrow band transmitter 404 configured to communicate with the narrow band receivers 306 included in sensors 504, and a wideband receiver 406 configured to receive signals from the wideband transmitters 304 included sensors 504. Again, gateway 502 can include a single antenna 402 or dual antennae. In fact, since gateway 502 is less resource constrained, it may be feasible and preferable to include separate transmit and receive antennae.

Both processor 408 and memory 410 can be larger and more powerful than the corresponding processor 308 and memory 310 included in sensors 504.

Gateway 502 can also include a power input that can provide power from an external supply such as the building or enclosures power system. It will be understood that power input block 414 can include some or all of the power circuits required, such as power conversion, regulation, over voltage protection, etc. Because power is not a concern for gateway 502, power input 414 can be configured to provide high power levels to both transmitter 404 and receiver 406. This allows transmitter 404 to transmit with significantly high power such that low power sensors 504 can still effectively receive the transmit signals even though they have very low power receivers. Similarly, receiver 406 can be supplied with very high power allowing it to receive and detect information included in the very low power signals received from low power transmitters 304.

One of skill in the art will understand the basic techniques and designs required to implement a sensor and a gateway as described, and in particular the receivers and transmitters circuits required. Although, specific coding and decoding algorithms, modulation techniques, etc., needed for optimum performance are not necessarily straight forward.

Figure 12:
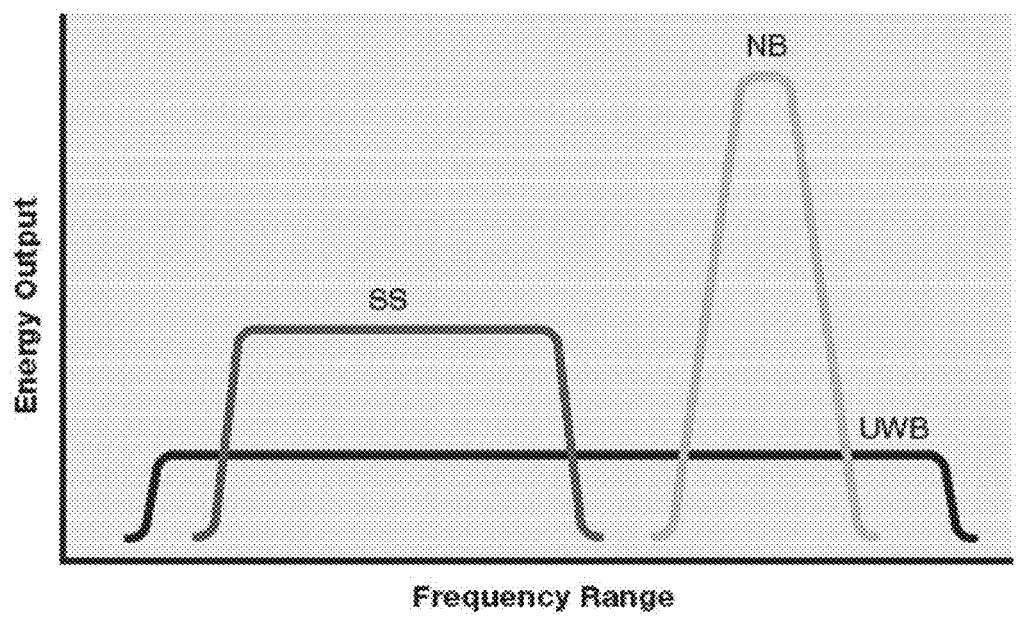
FIG. 12 is a diagram demonstrating the bandwidth and frequency ranges of UWB, narrow band, and spread spectrum systems.

Thus, the system can be a dual band system, i.e., a higher powered, narrow band system in the down link, and a low power, wide band system in the up link. Thus, a narrow band communication system/protocol, e.g., in the 2.4 GHz Industrial Scientific and Medical (ISM) band can be chosen for the down link portion. Ultra-WideBand (UWB) can be chosen for the uplink. FIG. 12 is a diagram demonstrating the bandwidth and frequency ranges of UWB, narrow band, and spread spectrum systems. As can be seen, the UWB signal comprises a very wide bandwidth and very low power compared, e.g., to the narrow band signal.

Accordingly, in certain embodiments, sensors 504 can comprise a low power low cost device comprising a UWB transmitter 304 and a narrowband ISM receiver 306, and gateway 502 can comprise a UWB receiver 406 and a narrowband ISM transmitter 404. The UWB frequency band is very wideband and is used for providing sensor data whereas the narrowband spectrum is used for control and data communication. The gateways 102 are connected to a backbone network and are highly synchronized. This allows gateways 102 to provide timing to sensors 504, so that sensors 504 do not require high cost, precision crystals.

Various implementations of UWB technology differ in frequency band and signal characteristics. The most common UWB technology is based on the WiMedia Alliance recommendations. WiMedia's UWB technology is an ISO-published radio standard for high speed wireless connectivity. UWB offers an unsurpassed combination of high data throughput and low energy consumption using bands within the frequency range of 3.1-10.6 GHz in the U.S. and many other parts of the world.

Figure 13:
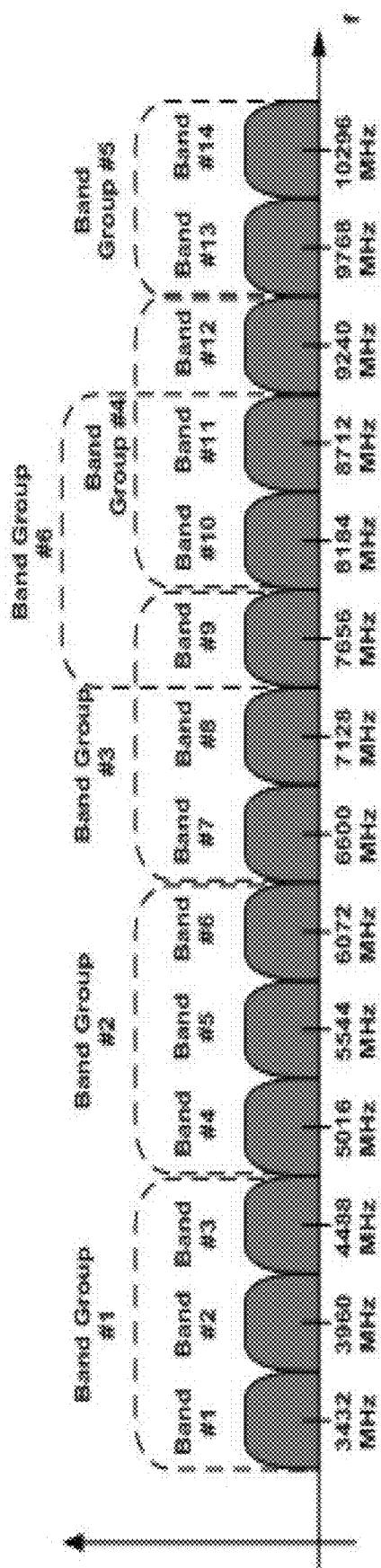
FIG. 13 is a diagram illustrating how the UWB physical layer divides the spectrum.

On the physical layer, the spectrum is divided into 14 bands and 6 band groups, each band group consisting of 3 bands as illustrated in FIG. 13. The WiMedia standard also specifies a multi-band orhtogonol frequency division multiplexing with or 110 sub-carriers per channel, i.e., 4.125 MHz bandwidth per sub-carrier, a channel bandwidth of 528 MHz and very low broadcast power that allows same cahnnel coexistence with narrower band devices such as 802.11a/b/g/n radios. UWB's much high bandwidth results in higher data throughput, coupled with a very low RF output power. UWB typically offers a communication range of up to 30 feet.

Figure 14:
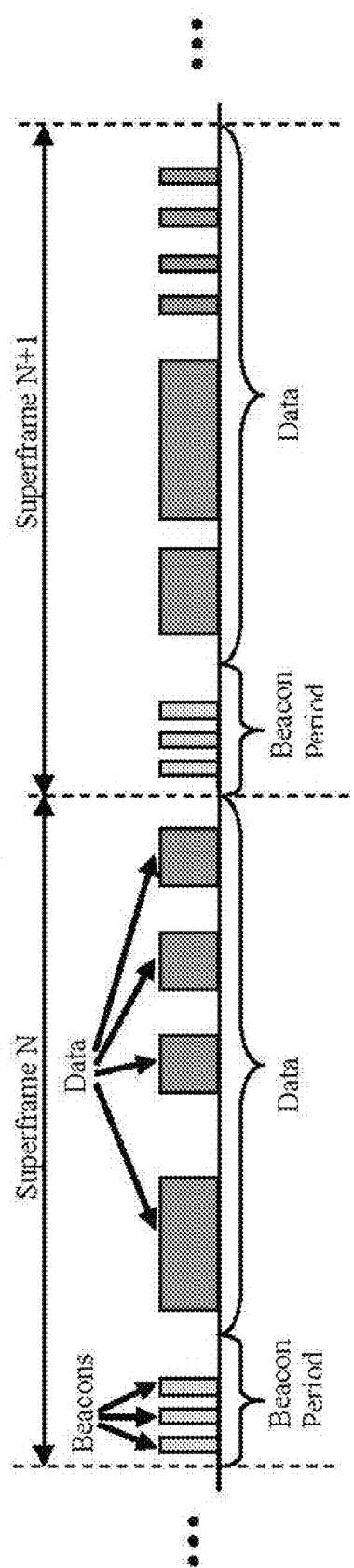
FIG. 14 is a diagram illustrating an example superframe of a UWB system.

The basic UWB timing for the network is the superframe. The superframe consists of a "beacon-period" and a "data period" that includes fixed duration time-slots as illustrated in FIG. 14. The beacon frame is transmitted by each UWB sensor 504 to ensure cooperative behavior among all sensors. The beacon frame provides basic timing information such as superframe start time as well as conveying reservation and scheduling information for medium access.

In certain embodiments, during a time slot in the data period, a sensor 504 can transmit a sensor data frame in the UWB spectrum. For example, a sensor 504 can broadcast its sensor data frame, which can be picked up by gateway 502. The sensor data frame can include a time stamp that indicates when the frame was sent.

As mentioned, the sensors 504 can comprise low cost, low precision crystals. Accordingly, the crystals will drift and the timing on sensors 504 will be off. But the gateway can transmit super frame timing information to the sensors 504, which can allow the sensors 504 to reset their timing and eliminate any such timing skew or drift.

The basic protocol can include the sensors 504 transmitting their sensor data frame, using the UWB spectrum, and the gateways 102 transmitting acknowledgement frame in return, using the narrow band spectrum. The acknowledgment frame can comprise timing and other information that allows the sensors 504 to reset their timing.

The sensor data frame can comprise at least a preamble and a header, and an optional data portion depending on the implementation. The frame can be modulated using ternary modulation, i.e. +1, 0, and −1 with a predetermined PRF (Pulse Repetition Frequency). The header can comprise a device ID field, possibly a time stamp, and can be encoded and protected with a CRC. The preamble can comprise a sync field and a start frame delimiter field. Each of these two fields can comprise data spread using a common spreading sequence. The common spreading sequence may consist of a ternary sequence with good correlation properties such as Ipatov and Justesen ternary sequence. Different sensors 504 can use a common ternary sequence or different ternary sequences depending on the implementation.

Further reductions in power can be achieved in sensors 504 by turning-on the UWB transmitter 304 only during the time-slot where the sensor 504 is attempting to send the sensor data and shutting down the transmitter 304 after finishing the frame transmission. A gateway 502 has a much higher complexity and has to be able to receive and demodulate frames sent from multiple sensors 504 typically during different time slots. A more advanced gateway 502 can be able to demodulate frames sent in the same time-slot as well.

In certain embodiments, after sending the sensor data frame, the sensor 504 waits for a predetermined period and turns on its narrow-band receiver 306 and waits for an acknowledgment frame from one or more gateways 102. In addition to successfully acknowledging successful reception of the frame, the acknowledgment frame can comprise control data and information data sent by the gateway 102.

If a sensor 504 does not receive an acknowledgment within a given time-out period, the sensor 504 can wait for a random time and attempt retransmission of the positioning packet in a different time-slot. The time-slot number can, e.g., be based on slotted-aloha protocol with exponential backoff.

As noted, timing can be established using a superframe structure established by the gateway 502 in the narrowband spectrum. The superframe is divided into two parts: A beacon period; and a time-slotted period. The beacon period can be divided into equal size time-slots. During a beacon time-slot, the gateway 502 can transmit a beacon frame comprising information about superframe timing and the structure of the superframe. If there are more than one gateway 502, then different gateeways can use different time-slots of the beacon and do not overlap with each other. The beacon frame can comprise as well time 0 of the UWB time axis that sets the time-slots boundary in the UWB spectrum. Thus, using this information, the sensors 504 can maintain proper timing. Further, the acknowledgement frame sent by the gateway 502 in a response to the positioning frame should be aligned with the boundary of a time-slot in the time-slotted narrowband superframe.

Figure 15A:
FIGS. 15A-C illustrate example wearable UWB MIR devices that can be included in the system of FIG. 5.
Figure 15B:
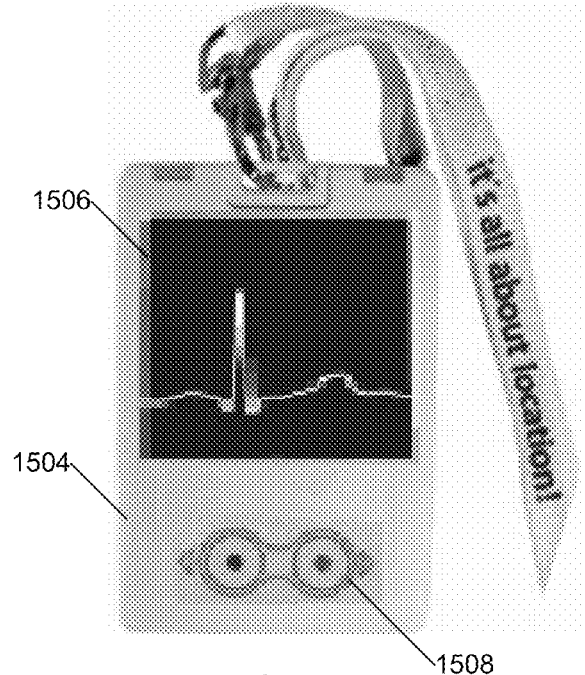
Figure 15C:
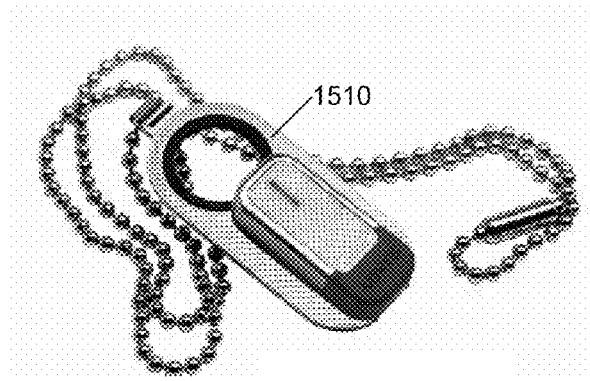

In certain embodiments Ultra Wide Band (UWB) MIR imaging sensors can also be included in system 500. Using the techniques described below, these sensors can be made smaller, last longer and cost less than a conventional MIR sensor. FIGS. 15A-C illustrate various embodiments of a UWB MIR imaging sensor as described herein. In FIG. 15A, sensor 1502 is included in a device that is about the size of a conventional access card. I FIG. 15B, device 1504 is larger than device 1502, but includes a display 1506 and controls 1508. In FIG. 15C, device 1510 is smaller than sensor 1502 in many dimensions. Sensors 1502, 1504 and 1510 are configured to be worn over the cloths and to sense various aspects such as heart rate, respiration, etc.

As explained above, a MIR device works by transmitting very narrow pulses, in this case into the body, and then detecting the echoes, which can be used to determine the shape and movement of various organs, skeletal structures, etc.

Figure 16:
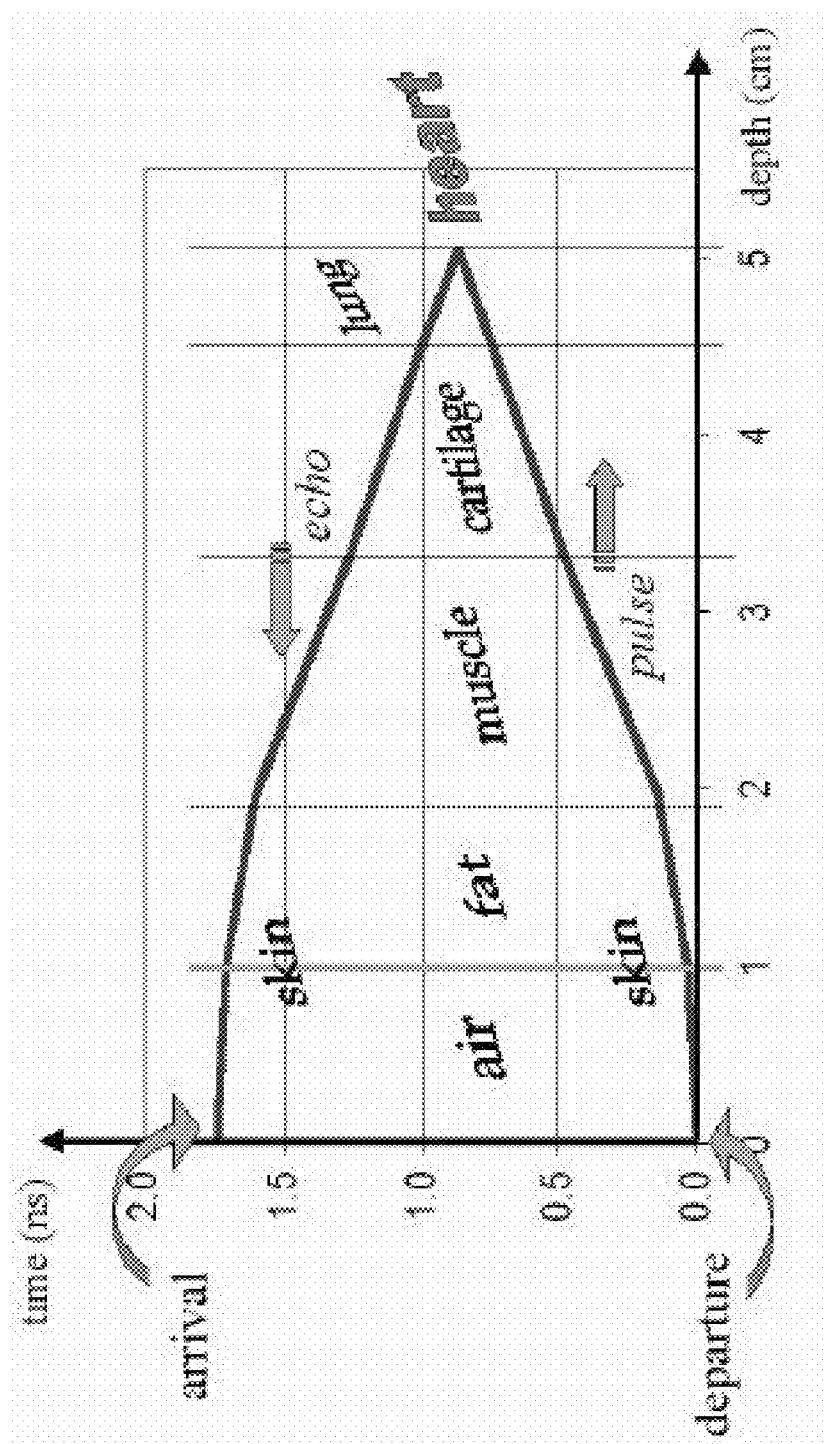
FIG. 16 is a diagram illustrating the propagation and echo of a signal transmitted into the body using the devices of FIGS. 15A-C.

FIG. 16 is a diagram illustrating the UWB pulse-echo delay times in the thorax.

Figure 17:
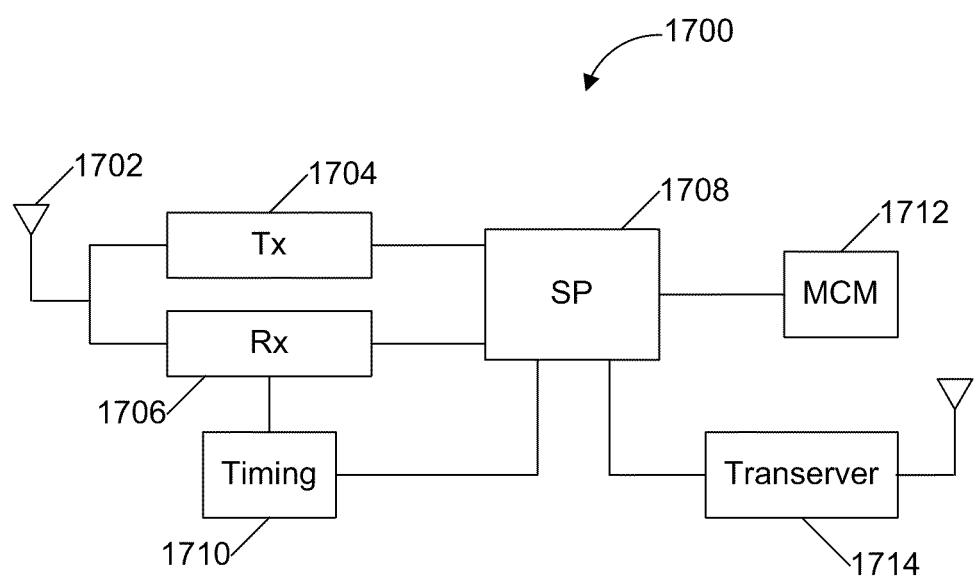
FIG. 17 is a block diagram illustrating an example UWB MIR devices in accordance with one embodiment.

FIG. 17 is a block diagram illustrating an example UWB MIR imaging sensor 1700 in accordance with one embodiment. As can be seen, sensor 1700 includes antenna 1702 for transmitting the narrow pulse signals and receiving the echoes, a transmitter 1704 than can include a pulse generator, a receiver 1706 with a pulse detector, timing circuitry 1710 for controlling the timing, a signal processor 1708 for processing the received echoes, memory 1712 for storing instructions and data, and a transceiver 1714 fro communicating the sensed data to, e.g., gateway 502.

In certain embodiments, a very narrow pulse is used in transmitter 1704 along with very precise timing controlled by timing circuitry 1710; however, in other embodiments, a spread signal can be used. Because the distance is short, a very low power signal, e.g., les than −10 db can be used. But this requires specific processing in signal processor 1708 to retrieve the data.

In certain embodiments, Golay codes can be used. A matched filter and thresholding can then be used to determine the peaks, or relevant information in the echoes and the relevant data can be compared to previous data to determine if there is a difference in the data. Only the differences can then be stored and communicated. In this way, lower processing and memory requirements are needed.

In certain embodiments, the data can be stored and then timing can be extracted from the digital data.

Transceiver 1714 can use the techniques described above to provide extremely low power operation. As a result of the techniques described herein, sensors 504 and 1700 can be implemented in low power System On Chip (SOC) designs that use low-powered radios and printable antennae, batteries, other circuits, or some combination thereof It should also be noted that transmitter 1704 and receiver 1706 can also be 60 GHz transmitters and receivers or even 90 GHz transmitters or receivers.

The imaging sensors described herein can be used to sense heart rate, cardiac volume, respiration rate, amniotic fluid levels, pneumothorax, pulmonary edema, head and other internal hemorrhage detection, and blood pressure measurements. This data can be used to perform cardiac biomechanics assessment, obstructive sleep apnea monitoring, soft tissue biomechanics research, skull imaging, heart imaging, chest imaging, etc. Further, a phase array of SOCs can be used to perform tomographic image recognition.

Figure 18:
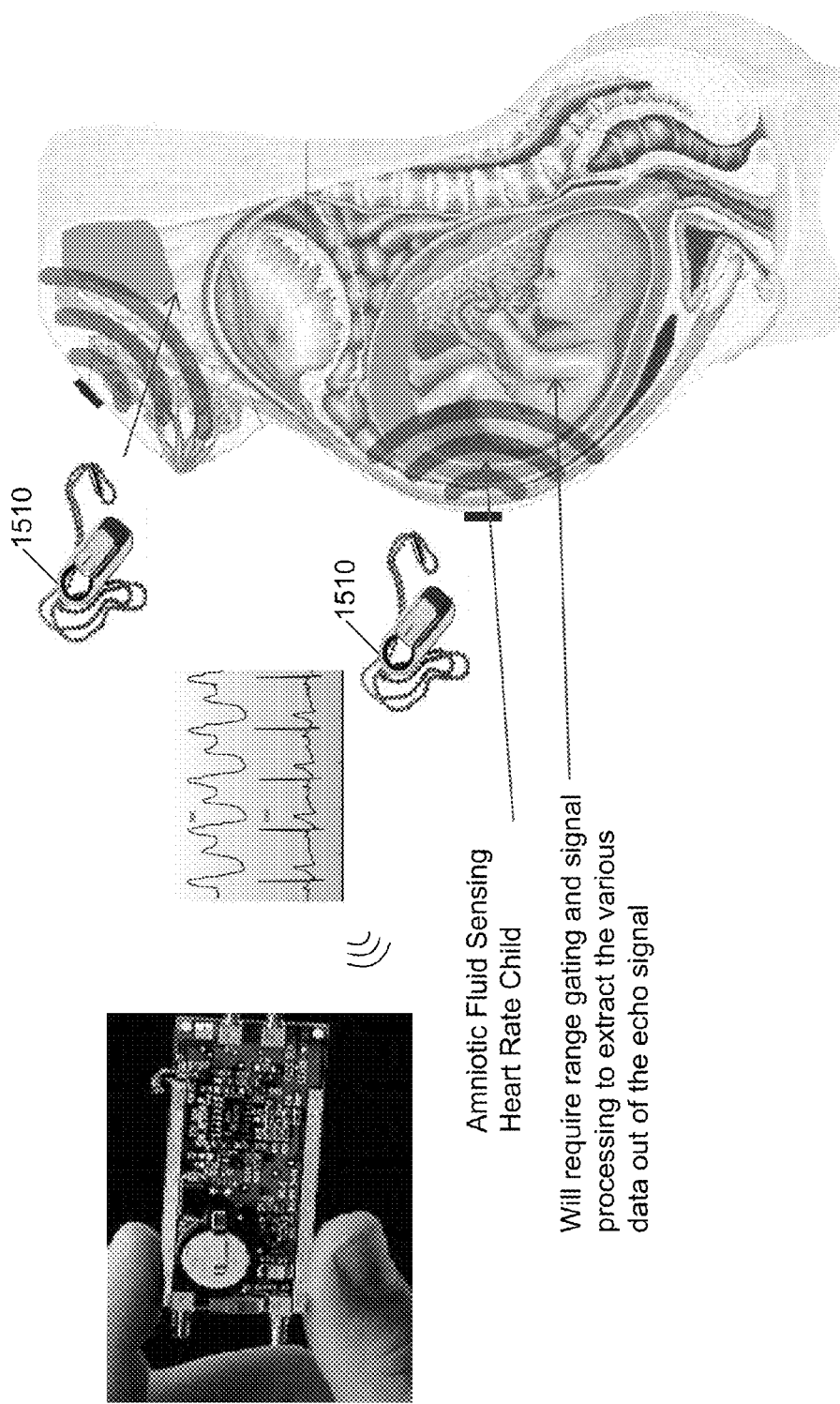
FIG. 18 is a diagram illustrating the use of the device of FIG. 15C to perform fetal monitoring.

FIG. 18 is a diagram illustrating the use of sensor 1510 to monitor a mothers heart rate and respiration rate as well as sense the amniotic fluid volume and heart rate of the baby. Such small, easy to use sensors can allow a mother to stay at home and avoid unneeded visits or time in the hospital or doctor's office but also inform as to when the mother should head to the hospital or doctor's office.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed:

1. A medical sensor system comprising:
a gateway comprising a wideband receiver and a narrow band transmitter, the gateway configured to receive a wideband positioning frame using the wideband receiver from one or more wearable sensors and to transmit acknowledgement frames using the narrow band transmitter that include timing and control information for use by the one or more wearable sensors to establish timing for transmission of the positioning frame; and
at least one of the one or more wearable sensors comprising a wideband transmitter and a narrow band receiver, the at least one wearable sensor configured to transmit a sensor data frame to the gateway using the wideband transmitter and to receive the acknowledgement frame from the gateway using the narrow band receiver, extract the timing and control information from the acknowledgment frame, and adjust timing and synchronization of the wideband transmitter using the timing and control information.

2. The system of claim 1, wherein the narrow band transmitter and the narrow band receiver are configured to operate in the Industrial Scientific and Medical (ISM) band.

3. The system of claim 2, wherein the narrow band transmitter and the narrow band receiver are configured to operate at about 2.45 GHz.

4. The system of claim 1, wherein the wideband receiver and the wideband transmitter are configured to operate in the Ultra Wideband (UWB) spectrum.

5. The system of claim 1, wherein the gateway is configured to transmit, using the narrow band transmitter, the timing and control information for the wideband transmitter operation.

6. The system of claim 5, wherein the at least one wearable sensor is configured to receive the timing and control information, synchronize the wideband transmitter and transmit the positioning frame.

7. The system of claim 6, wherein the gateway is configured to receive the sensor data frame and send information included in the sensor data frame to a remote location.

8. The system of claim 6, wherein the at least one wearable sensor uses a superframe to communicate with the gateway via the wideband transmitter, and wherein the timing and control information includes super frame information including the start time of the superframe.

9. The system of claim 1, wherein the at least one wearable sensor is configured to turn on the wideband transmitter for a short duration in order to transmit the positioning frame and then turn the wideband transmitter off.

10. The system of claim 9, wherein the at least one wearable sensor is further configure to then turn the narrow band receiver on for short period in order to receive the acknowledgement frame form the gateway and then turn the narrow band receiver off.

11. The system of claim 10, wherein the at least one wearable sensor is configured to attempt re-transmission of the positioning frame when it does not receive an acknowledgement in a certain period of time.

12. The system of claim 1, wherein the at least one wearable sensor is a temperature sensor.

13. The system of claim 1, wherein the at least one wearable sensor is a UWB MIR imaging sensor.

\* \* \* \* \*